United States Patent [19]

English et al.

[11] Patent Number: 4,901,144

[45] Date of Patent: Feb. 13, 1990

[54] VIDEO ENDOSCOPE APERTURE WHEEL DRIVE SYSTEM

[75] Inventors: Stanley R. English, Elbridge; David R. McKenzie, Auburn, both of N.Y.

[73] Assignee: Welch Allyn, Inc., Skaneateles Falls, N.Y.

[21] Appl. No.: 221,650

[22] Filed: Jul. 20, 1988

[51] Int. Cl.[4] .......................... A61B 1/04; A61B 1/06; H04N 5/238

[52] U.S. Cl. ....:................................. 358/98; 128/6; 358/168

[58] Field of Search ...................... 358/98, 168; 128/6

[56] References Cited

U.S. PATENT DOCUMENTS

| | | | |
|---|---|---|---|
| 4,523,224 | 6/1985 | Longacre | 358/42 |
| 4,532,918 | 8/1985 | Wheeler | 128/6 |
| 4,539,586 | 9/1985 | Danna | 358/98 |
| 4,546,379 | 10/1985 | Sarofeen | 358/98 |
| 4,653,478 | 3/1987 | Nagasaki | 358/98 |

Primary Examiner—Howard W. Britton
Attorney, Agent, or Firm—Wall and Roehrig

[57] ABSTRACT

A video endoscope aperture wheel drive system effective to position a predetermined aperture formed in an aperture wheel in an optical path of an image generated by an imaging device viewing an object, while eliminating oscillation of the aperture wheel caused by the rotational stepping of the aperture wheel in either direction in response to movement of a video probe in which an imaging device is positioned. The aperture wheel motor is rotated clockwise or counter-clockwise in response to the proximity of the imaging device relative to the object being viewed.

5 Claims, 3 Drawing Sheets

VIDEO ENDOSCOPE APERTURE WHEEL DRIVE SYSTEM

BACKGROUND OF THE INVENTION

This invention relates in general to video endoscope aperture wheel drive systems and, in particular, to a drive system for stepping the position of an aperture wheel used in devices for generating video images.

More specifically, but without restriction to the particular embodiment and/or use which is shown and described for purposes of illustration, this invention relates to a drive system for an aperture wheel used in a video processor for generating video images which eliminates oscillation of the aperture wheel when being advanced or stepped to a desired position in accordance with the operation of an aperture wheel stepping motor.

In video image generating systems, such as a video-equipped endoscope or borescope, a light source is utilized for illuminating an object in order to generate a video image. The light source is projected onto the object, and the light reflected from the object is received by a viewing head of a viewing probe which focuses an image upon an imaging device within the probe. Upon receipt of the reflected image, the imaging device converts the image into electrical signals for further processing. For a more detailed description of such imaging systems, reference is made to the disclosures in Robert C. Wheeler, U.S. Pat. No. 4,532,918 and Dominick Danna et al. U.S. Pat. No. 4,539,586 the disclosures of which are hereby incorporated by reference.

The systems disclosed in these above-identified patents, or other such video imaging systems, may utilize a light control wheel in the form of a color filter wheel or a chopper wheel which functions as a shutter between the light source and viewing probe. In those applications in which a color filter wheel is utilized, the color wheel is positioned to selectively rotate a series of different colored filters in the light path to the imaging device to thereby produce a series of color separated images which are sequentially transmitted to the target area of the imaging device. This series of color separated images produces a field sequential color video signal.

In order to generate the sequence of color images, the color filter wheel includes a plurality of color filters circumferentially spaced in an equidistant pattern. The spaces between the color filters do not permit any light transmission, but function as a shutter for preventing light transmission during rotation of the color filter wheel between adjacent filter segments. During the time in which light transmission is blocked, the color separated images received by the imaging device are read out through conventional video processing circuitry. Such a process is disclosed in U.S. Pat. Nos. 4,546,379 and 4,523,224, the disclosures of which are incorporated herein by reference.

In certain applications a color separated imaging system is not necessary nor is it preferred. In such black and white video systems, the light from the light source is transmitted to an object to be viewed, and the light reflected from that object is received by the viewing head of a viewing probe in the manner previously described. In order to enable the video processing circuitry to read the image reflected onto the imaging device within the probe, however, the light must be interrupted in the manner previously described. This light interruption function is affected by the use of a chopper wheel having portions removed which permit the passage of light, with adjacent light blocking or shutter portions enabling the video processing circuitry to read the image projected onto the imaging device during the time the light transmission is interrupted.

When utilizing an imaging system in an endoscope or borescope application, it has been found that a color system has optimum performance within a particular range of distances between the imaging device and the object to be viewed, and a black and white video system has a different optimum performance viewing range. However, in both systems the intensity of the light being received by the video imaging system through the probe must be monitored and controlled for optimum endoscope and/or borescope applications. To this end, an aperture wheel is interposed in the light path between the object to be imaged and the video imaging system in order to control the intensity of the light received from the imaging device. Because the probe may be positioned at different distances from the object being imaged, the intensity of the light reflected onto the probe and transmitted thereby to the video imaging system will vary with the proximity of the imaging device to the object being imaged.

The intensity of the light reflected from the object being viewed can be controlled by the use of different sized apertures, and the interposing of different sized apertures into the light path in response to the proximity of the viewing probe to the object being imaged will produce a substantially uniform light intensity applied to the video imaging system.

The aperture wheel is formed with various sized openings positioned thereon such that rotation of the aperture wheel will sequentially position each of the apertures formed therethrough in optical alignment with the video imaging system. In this manner the intensity of the light reflected onto the imaging device of the probe is controlled by rotation of the aperture wheel, bringing the desired aperture into optical alignment so that the video imaging system has the desired amount of light to be received. As is known to those skilled in the art, the rotational positioning of the aperture wheel may be automatically controlled in response to the proximity of the object being viewed or the intensity of the reflected light.

Because the probe bearing the imaging device is moved relative to the object being viewed, the light reflected from the object into the probe imaging device varies with the proximity of the probe to the object. In order to maintain a pre-determined desirable light intensity on the imaging device probe, the aperture wheel must be rotated for changing the aperture interposed in the light path to the video imaging system in response to these variations in light intensity. Various control systems are known to those skilled in the art for providing a control signal which can be coupled to an aperture wheel drive motor for energizing the motor to rotate or step the aperture wheel in response to changes in the light intensity which, for example, is reflected back from the object being viewed.

Because the probe is moved fairly rapidly to different viewing positions, the aperture wheel must respond quickly in order to control the light intensity to the video imaging system. For this reason the aperture wheel is generally formed from a thin light-weight material which permits rapid movement or indexing of the aperture wheel without creating large inertia forces.

One of the problems associated with rapid movement or stepping of the aperture wheel is oscillation, which is caused by the inertia of the wheel itself, or the inertia of the mechanisms which are used to effect stepping of the aperture wheel in response to movement of the probe. Heretofore, aperture wheel drive systems wherein the aperture wheel was mounted directly on the drive shaft of a stepping motor to effect rotation or stepping of the aperture wheel in either direction, the inertia of the motor armature and the aperture wheel caused oscillation of the aperture wheel after the motor was stopped. Such oscillations degrade the quality of the picture on the video imaging system, causing quite noticeable and undesirable flicker or cyclic increase and decrease in the brightness of the picture. One attempt to eliminate this degradation in picture quality has been the use of a friction clutch on the motor drive shaft. Such an attempt, however, was not satisfactory in that it did not provide consistent results.

The aperture wheel must be accurately positioned to insure that the predetermined aperture is interposed in the optical path in response to the positioning of the probe. The aperture wheel drive system, therefore, must not only eliminate oscillation of the aperture wheel, but accurately control the rotational position of the aperture wheel so that the desired aperture is interposed in the optical path to the video imaging system in response to the distance between the probe imaging device and the object being viewed, or the intensity of the reflected light, so that the system can be coordinated to stop the aperture wheel in the predetermined position.

SUMMARY OF THE INVENTION

It is, therefore, an object of this invention to improve light attenuators for video endoscope systems.

Another object of this invention is to improve the drive system for an aperture wheel used to control the intensity of light applied from an imaging device carried in a video probe.

A further object of this invention is to eliminate or minimize oscillation of a video system aperture wheel to improve the quality of the transmitted video picture.

Still another object of this invention is to accurately position the oscillation-free aperture wheel in the optical path between an object being viewed and the imaging device of a video probe to enhance the quality of the transmitted picture.

These and other objects are attained in accordance with the present invention wherein there is provided a video endoscope aperture wheel drive system effective to position a predetermined aperture formed in an aperture wheel in an optical path of an image generated by an imaging device viewing an object, while eliminating oscillation of the aperture wheel caused by the rotational stepping of the aperture wheel in either direction in response to movement of a video probe in which an imaging device is positioned. The aperture wheel motor is rotated clockwise or counter-clockwise in response to the proximity of the imaging device relative to the object being viewed.

BRIEF DESCRIPTION OF THE DRAWING

Further objects of the invention together with additional features contributing thereto and advantages occurring therefrom will be apparent from the following description of a preferred embodiment of the invention which is shown in the accompanying drawings with like reference numerals indicating corresponding parts throughout, wherein.

DETAILED DESCRIPTION OF THE PREFERRED EMBODIMENT

Figure 1:
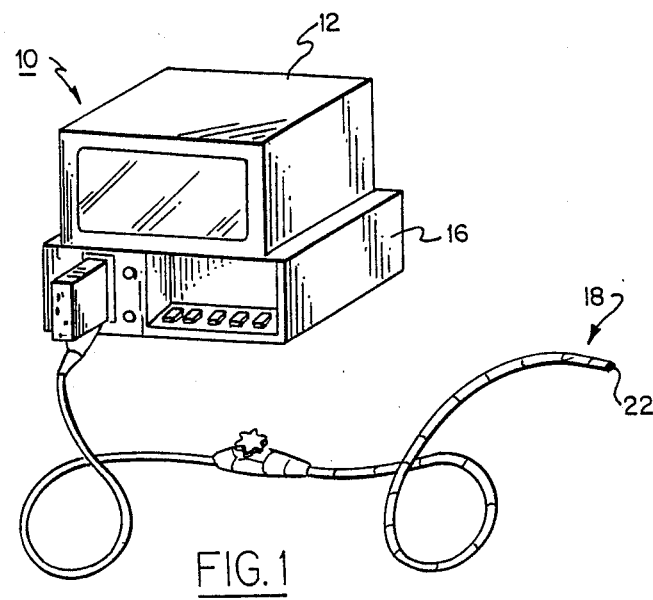
FIG. 1 is frontal perspective view of a video endoscope including a probe having an imaging device for generating a picture of an object to be viewed.

Referring now to FIG. 1, there is shown a video endoscope system 10 incorporating the invention. The video endoscope system 10 includes a video monitor 12, a video processor 16, and a viewing probe 18. The viewing probe 18 has at its distal end 22, a known type of solid state imaging device such as a virtual phase charge coupled imaging device, or CCD. A detailed description of a suitable video endoscopic system 10 in which the present invention may be incorporated is described in U.S. Pat. Nos. 4,532,918 and 4,539,586 referred to previously.

Figure 2:
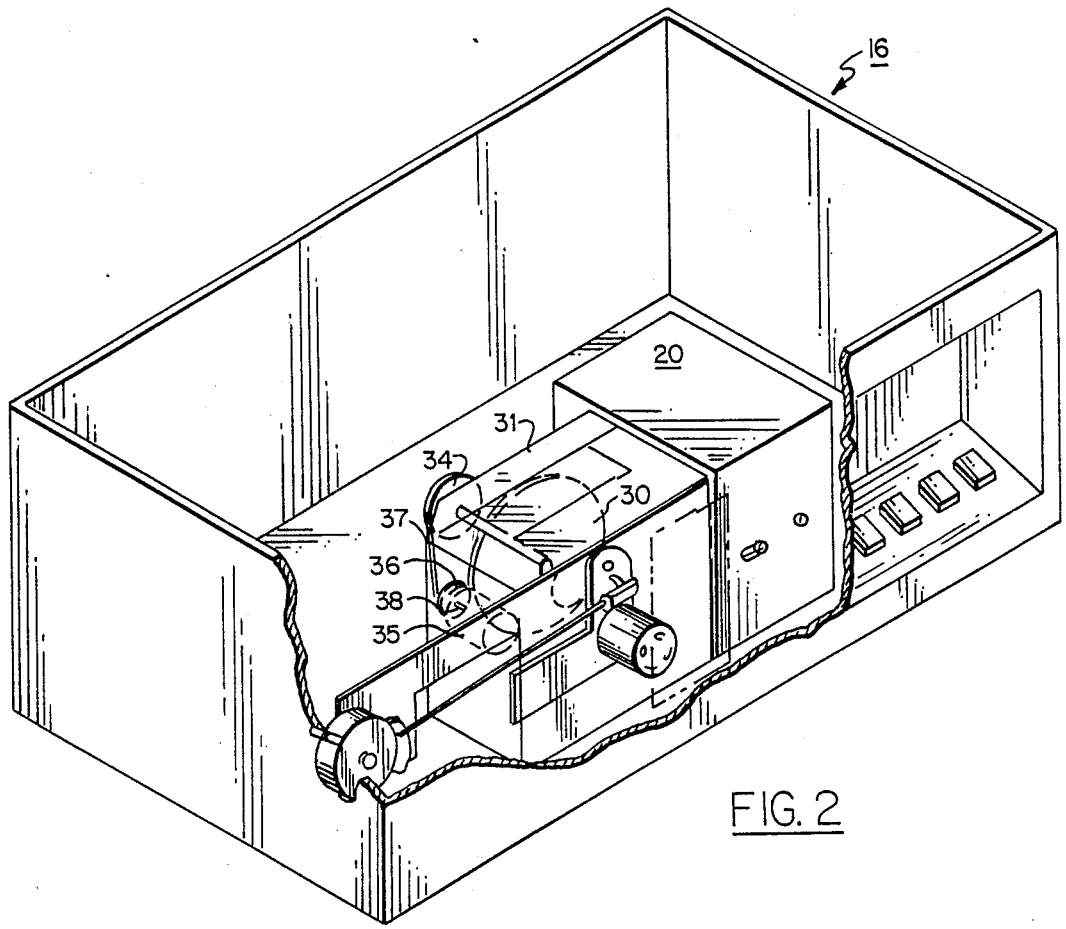
FIG. 2 is an enlarged perspective view of a portion of the video processor, with parts removed, to better illustrate the manner in which an aperture wheel is positioned in the optical path of the video processor.
Figure 3:
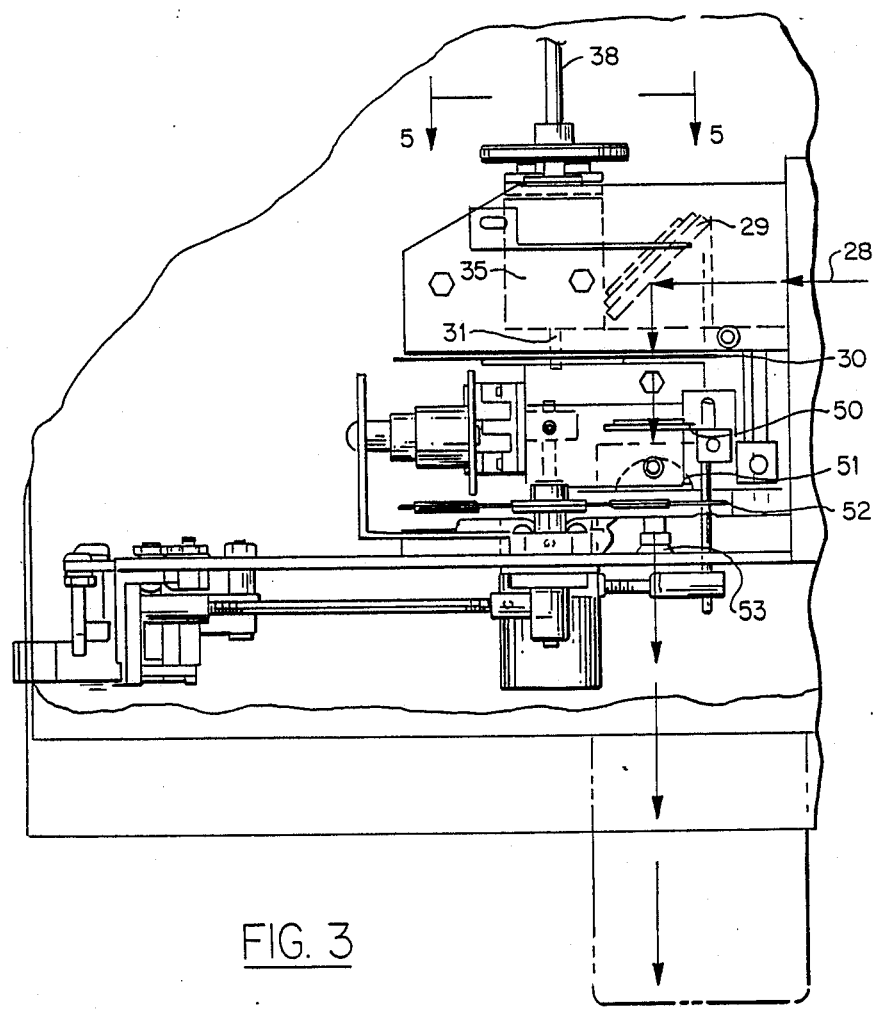
FIG. 3 is an enlarged horizontal planar view of a portion of the video processor to better illustrate the optical path components.

The video endoscope 10 includes an image generation system 20 having a light source 28 used in cooperation with the viewing probe 18. As shown in FIGS. 2 and 3, the light source 28 emits a light beam that is deflected approximately 90 degrees by a mirror 29. Mirror 29 directs the light beam along an optical path passing through an aperture wheel 30, an infra-red filter 50, allens 51, a light control wheel 52, and a clear aperture 53, to optically couple the light beam to viewing probe 18. Light reflected from the object being viewed is received by viewing probe 18, which causes an image to be focused upon the solid state imaging device, CCD, located therein. The imaging device or CCD receives the image and converts it into electrical signals to be processed.

In order to maintain uniform intensity of the reflected light, the aperture wheel 30 is positioned relative to the optical path to interpose a predetermined opening or aperture in response to the intensity of the reflected light. To this end, aperture wheel 30 is formed as a light weight disk containing a plurality of apertures therethrough. The aperture wheel 30 is mounted on a shaft 31 allowing it to be rotated to a plurality of positions to regulate the intensity of the light beam. For further information concerning the manner in which the video endoscope functions and additional details as to components of the optical system, reference is made to a co-pending application filed concurrently herewith in the names of Stanley R. English and Dominick Danna, entitled "Apparatus for Converting a Video Processor", the disclosure of which is incorporated herein by reference, Ser. No. 07/221,776.

Figure 4:
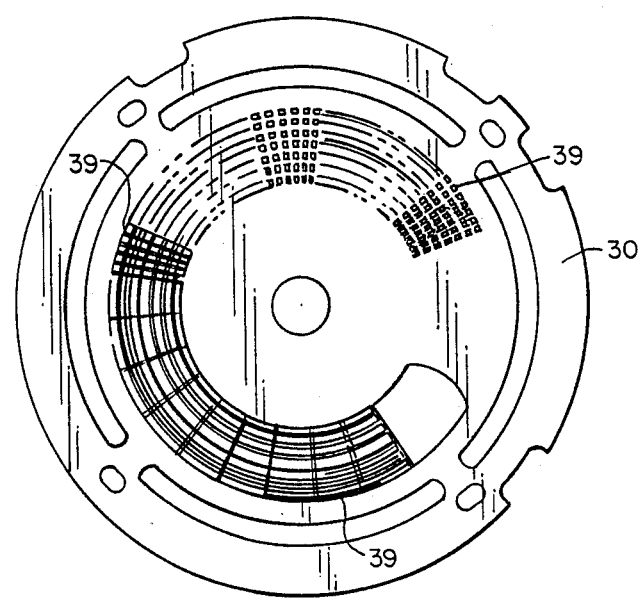
FIG. 4 is a vertical planar view of an aperture wheel used to control light intensity.
Figure 6:
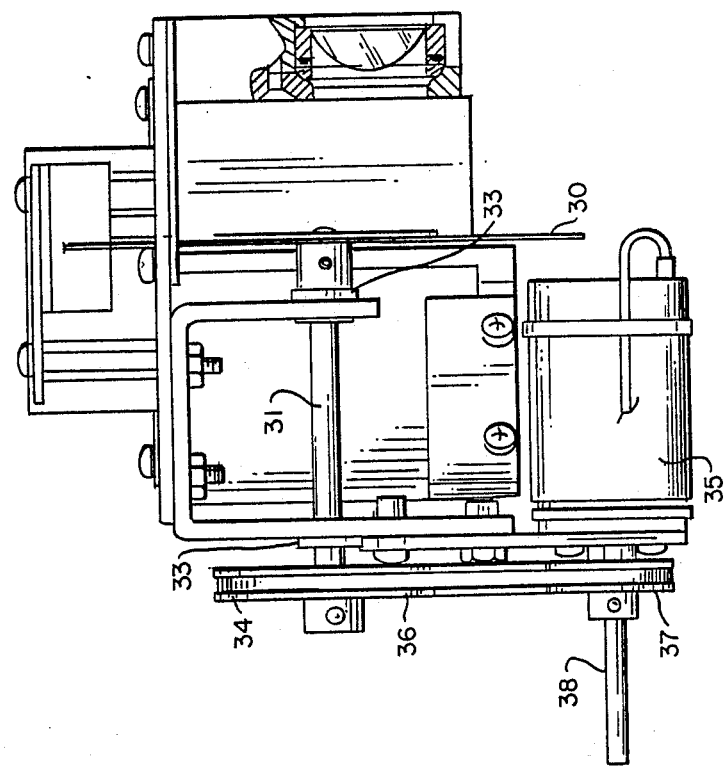
FIG. 6 is an enlarged view of the apparatus illustrated in FIG. 3 taken along lines 6—6.
Figure 5:
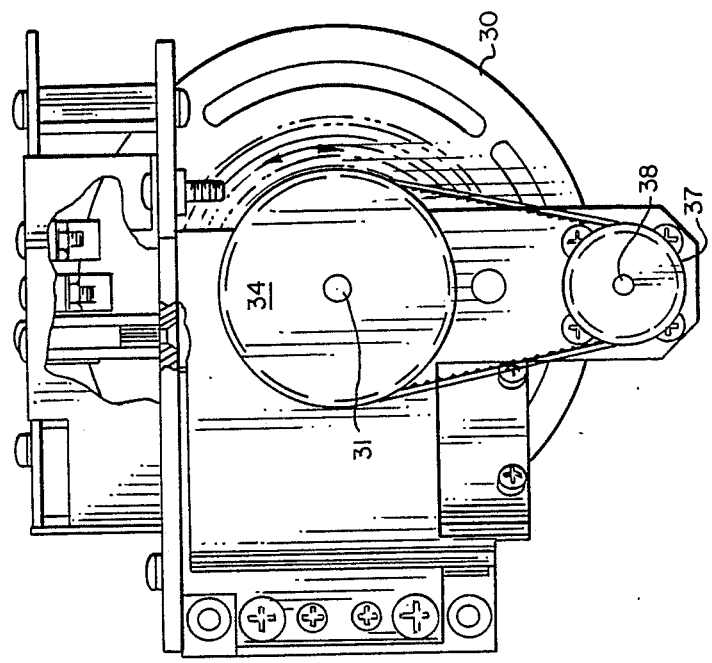
FIG. 5 is an enlarged view of the apparatus illustrated in FIG. 3 taken along lines 5—5.

Referring also to FIGS. 4–6, the aperture wheel 30 is formed with a plurality of different sized openings 39 which are formed in a logarithmic pattern to provide a uniform light intensity reduction between adjacent stepped positions when the aperture wheel 30 is stepped throughout its positioning sequence. The shaft 31 upon which the aperture wheel 30 is positioned, is supported by means of a bracket 32 in which the shaft 31 is supported for rotation by a pair of bushings 33. The outboard end of the shaft 31 has connected thereto a driven gear 34 which functions to rotate the aperture wheel 30 in a clockwise or counter-clockwise direction to position a particular aperture into the light path.

Control of the aperture wheel 30 position is effected by means of a stepping motor 35 which is coupled to the aperture wheel shaft 31 by means of a timing belt 36 which engages a drive gear 37 secured to the output or drive shaft 38 of the stepping motor 35.

In operation, as the probe 18 is positioned relative to an object to be viewed, the light reflected back from the object will vary with the distance between the probe 18 and the object. Accordingly, a control system of various types known to those skilled in the art is utilized to provide a feedback or control signal generated in response to the light intensity reflected back from the object being viewed. The control signal generated in response to the light intensity is coupled to the stepping motor 35 to effect the rotation thereof in a clockwise or counter-clockwise direction, depending upon whether the intensity is increasing or decreasing in response to the proximity of the probe to the object being viewed.

The stepping motor 35, when actuated, is rotated in predetermined increments, preferably fifteen degrees of rotation. Because the rotation of the stepping motor 35 is coupled to the aperture wheel 30 by means of the timing belt 36, the aperture wheel will be rotated in accordance with the stepping motor 35. Depending upon the relationship between the size of the drive gear 37 of the stepping motor 35 and the driven gear 34 of the aperture wheel shaft 31, the degree of rotation of the stepping motor 35 can effect a greater or lesser rotation of the aperture wheel 30. Because of this drive coupling, once the aperture wheel 30 has been positioned with a predetermined aperture interposed into the optical path, the actuation of the stepping motor 35 will be known to position another of the apertures formed in the aperture wheel in the optical path in accordance with the amount and direction of the stepping motor 35 rotation.

When the stepping motor 35 is actuated, the motor rotates a predetermined amount, preferably fifteen degrees and stops unless receiving further signals to continue rotation. When the motor 35 stops, a certain amount of inertia force is created by the mechanical movement. Heretofore, when an aperture wheel has been driven directly by the stepping motor, the direct drive coupling causes the aperture wheel to oscillate when the motor is stopped. These oscillations cause a "flutter" in the video image displayed on the video monitor due to this movement of the aperture wheel. The indirect coupling by means of the drive belt 36 eliminates transmitting of the stepping motor 35 inertia to the aperture wheel 30, thereby eliminating image degradation caused by aperture wheel oscillation resulting in no "flutter" of the video image.

While various timing belts 36 could be utilized, a thirty two pitch, 3/32 diameter, polyurethane cordless belt is preferred. Such a belt is available from Nordex of Danbury, Conn. under their model number FGD-D3-75. Another suitable supplier is Precision Industrial Components Corporation of Middlebury, Conn. The special pulleys or gears used with such a timing belt 36 are grooved, and the driving gear 37 mounted on the drive shaft 38 of the stepping motor 35 is preferably a 24-tooth driving gear available from Nordex under their model number FHA-D1-24. A preferable driven gear 34, which is secured to the aperture wheel shaft 31, is a 48-tooth driven gear available from Nordex under their model number FHA-D2-48. Because the driven gear 34 is twice as large as the stepping motor drive gear 37, when the stepping motor 35 is moved 15 degrees between null points, which is preferred, the aperture wheel 30 will, accordingly, be rotated 7-½ degrees. In this manner, the drive belt 36 times the system as well as isolates the aperture wheel 30 from the mechanical inertia forces generated by operation of the stepping motor 35.

While the invention has been described in the specification and illustrated in the drawings with reference to a preferred embodiment, it will be understood by those skilled in the art that various changes may be made and equivalents may be substituted for elements of the invention without departing from the scope of the claims. In addition, many modifications may be made to adapt a particular situation or material to the teachings of the invention without departing from the essential scope thereof. Therefore, it is intended that the invention not be limited to the particular embodiment illustrated by the drawings and described in the specification as the best mode presently contemplated for carrying out this invention, but that the invention will include any embodiments falling within the description of the appended claims.

What is claimed is:

1. In a video endoscope wherein a source of light is projected onto an object to be viewed and the light reflected from the object being viewed is received by an imaging device carried at the distal end of a viewing probe and the intensity of the light projected onto the object is varied by passing through an aperture wheel positioned in the optical path of the video endoscope, said aperture wheel being rotatable by a stepping motor to maintain a predetermined light intensity through the selective interposing of apertures formed in the aperture wheel into the optical path, the improvement comprising inertia force isolating drive means coupled between said stepping motor and said aperture wheel for effecting rotation of said aperture wheel in response to rotation of said stepping motor and isolating said aperture wheel from inertia forces generated by the rotation of said stepping motor when said stepping motor is rotated.

2. The apparatus defined by claim 1 wherein said inertia force isolating drive means includes a timing belt coupled to a drive gear mounted on a drive shaft of said stepping motor and to a driven gear mounted to a shaft upon which said aperture wheel is supported.

3. The apparatus defined by claim 2 wherein said timing belt controls the selecting interposing of said apertures formed in said aperture wheel into the optical path of the video endoscope in response to the rotation of said stepping motor.

4. The apparatus defined by claim 3 wherein said stepping motor is rotated in response to the intensity of light reflected by the object being viewed.

5. The apparatus defined by claim 3 wherein said stepping motor is rotated in response to the proximity of said viewing probe to the object being viewed.

* * * * *